United States Patent [19]
Kuczkowski et al.

[11] Patent Number: 5,310,921
[45] Date of Patent: May 10, 1994

[54] BIS-(2,5-POLYTHIO-1,3,4-THIADIAZOLES), RUBBERS CONTAINING SUCH COMPOUNDS, AND A METHOD OF PREPARATION OF BIS-(2,5-POLYTHIO-1,3,4-THIADIAZOLES)

[75] Inventors: Joseph A. Kuczkowski, Munroe Falls; Michael B. Rodgers, Akron; Kevin L. Rollick, Munroe Falls, all of Ohio

[73] Assignee: The Goodyear Tire & Rubber Company, Akron, Ohio

[21] Appl. No.: 935,324

[22] Filed: Aug. 26, 1992

[51] Int. Cl.$^5$ .................. C07D 513/18; C08K 5/46
[52] U.S. Cl. .................. 548/126; 525/333.1; 525/349
[58] Field of Search .................. 548/126; 525/333.1, 525/349

[56] References Cited

U.S. PATENT DOCUMENTS

| | | | |
|---|---|---|---|
| 3,087,932 | 4/1963 | Little et al. | 260/302 |
| 3,663,561 | 5/1972 | Blaha | 260/302 SD |
| 4,599,425 | 7/1986 | Hugo et al. | 548/142 |

FOREIGN PATENT DOCUMENTS

| | | | |
|---|---|---|---|
| 3330919 | 3/1985 | Fed. Rep. of Germany | 548/126 |
| 4013714 | 10/1991 | Fed. Rep. of Germany | 548/126 |

*Primary Examiner*—Robert Gerstl
*Attorney, Agent, or Firm*—Bruce J. Hendricks

[57] ABSTRACT

This invention relates to bis-(2,5-polythio-1,3,4-thiadiaxoles), a method for their preparation and their use in rubber compounds. Use of these compounds provide for excellent vulcanization of rubbers and result in an improved final rubber vulcanizate possessing good physical properties.

11 Claims, No Drawings

BIS-(2,5-POLYTHIO-1,3,4-THIADIAZOLES), RUBBERS CONTAINING SUCH COMPOUNDS, AND A METHOD OF PREPARATION OF BIS-(2,5-POLYTHIO-1,3,4-THIADIAZOLES)

BACKGROUND OF THE INVENTION

This invention relates to bis-(2,5-polythio-1,3,4-thiadiazoles) and their use in the vulcanization of natural rubber, a rubber derived from a diene monomer and mixtures thereof.

In the manufacture of rubber articles, crude or raw rubber is compounded with various ingredients among which are sulfur and accelerators. The primary function of an accelerator or accelerator system is to increase the rate of the vulcanization process while allowing sufficient time to mix the accelerators into the rubber at an elevated temperature before vulcanization commences. Many accelerator combinations have been used in the rubber industry. Unfortunately, many of the known accelerators, such as morpholine containing compounds, dimethyl amine containing compounds and dithiocarbamate compounds yield volatile nitrosoamines upon use. The use of compounds which yield volatile nitrosoamines have been significantly restricted in a number of countries and the need to find a suitable replacement is imminent.

SUMMARY OF THE INVENTION

The present invention relates to bis-(2,5-polythio-1,3,4-thiadiazoles) and their use in rubber stocks.

DETAILED DESCRIPTION OF THE INVENTION

There is disclosed bis-(2,5-polythio-1,3,4-thiadiazoles) consisting of the formula:

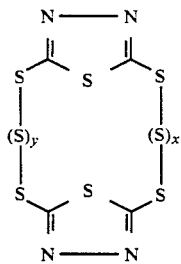

wherein the sum of x and y is from 1 to 16 and x and y are independently selected from 0 and integers of from 1 to 8.

There is also disclosed a process for accelerating the cure rate of a rubber stock comprising admixing (1) a rubber selected from the group consisting of natural rubber, synthetic rubbers derived from a diene monomer and mixtures thereof with (2) a bis-(2,5-polythio-1,3,4-thiadiazole) consisting of the formula:

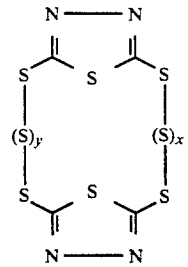

wherein the sum of x and y is from 1 to 16 and x and y are independently selected from 0 and integers of from 1 to 8.

There is also disclosed a rubber stock which comprises (1) a rubber selected from the group consisting of natural rubber, synthetic rubbers derived from a diene monomer and mixtures thereof, and (2) a bis-(2,5-polythio-1,3,4-thiadiazole) consisting of the formula:

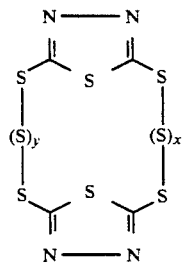

wherein the sum of x and y is from 1 to 16 and x and y are independently selected from 0 and integers of from 1 to 8.

The present invention also relates to a process for preparation of the above bis-(2,5-polythio-1,3,4-thiadiazoles) comprising reacting 2,5-dimercapto-1,3,4-thiadiazole and elemental sulfur in water with hydrogen peroxide at a temperature ranging from 20° C. to 100° C. wherein the molar ratio of 2,5-dimercapto-1,3,4-thiadiazole to hydrogen peroxide is 1:1 and the molar ratio of 2,5-dimercapto-1,3,4-thiadiazole to elemental sulfur ranges from 16:1 to 1:1.

The reaction product of the above reaction may consist of a mixture of bis-(2,5-polythio-1,3,4-thiadiazoles), all of which may vary in molecular weight. For example, referring to the above structural formula, there may be a mixture of the materials wherein x and y may range from 0 to 8 so long as the sum of x and y is at least 1 and up to 16. Preferably, x and y are integers ranging from about 2 to 4. The molecular weight of the reaction product will vary depending on the ratio of reactants, temperature of the reaction and reaction time. The molecular weight of the composition of the present invention may range from about 328 to about 808. Preferably, the molecular weight of the reaction product ranges from about 424 to 552.

In accordance with the process of making the bis(2,5-polythio-1,3,4-thiadiazoles), the mole ratio of 2,5-dimercapto-1,3,4-thiadiazole to sulfur may range from about 16:1 to 1:1. Preferably, the mole ratio ranges from about 4:1 to 2:1.

The mole ratio of 2,5-dimercapto-1,3,4-thiadiazole to hydrogen peroxide should range from about 1:1 to 1.5:1. Preferably, the mole ratio is from 1:1 to 1.25:1.

In accordance with the present invention, 2,5-dimercapto-1,3,4-thiadiazole and elemental sulfur in water are reacted with hydrogen peroxide. The term elemental sulfur is used herein to describe the $S_8$ or rhombic form of sulfur.

The reaction may be conducted over wide temperatures. In general, the reaction may be conducted at a temperature of from about 20° C. to about 100° C. Preferably, the condensation reaction is conducted at a temperature ranging from about 50° C. to about 95° C.

The reaction between the 2,5-dimercapto-1,3,4-thiadiazole, elemental sulfur and hydrogen peroxide may be conducted under a variety of pressures, with atmospheric pressure being preferred. The reaction may be conducted under an inert atmosphere or air. Preferably, the atmosphere is air.

The reaction is conducted for a time sufficient to produce the desired product which upon heating and isolation will result in the bis-(2,5-polythio-1,3,4-thiadiazole). In general, the reaction time may vary from about 1 hour to about 8 hours.

Upon completion of the reaction, the desired bis-(2,5-polythio-1,3,4-thiadiazole) is isolated. The method of isolation is conventional and well known to those skilled in the art and may consist of permitting the reaction mixture to cool for subsequent use or by simple vacuum filtration.

The bis-(2,5-polythio-1,3,4-thiadiazoles) may be used with a number of rubber stocks. While the utility of these materials in rubber stocks may vary depending on the amount used, the use as an accelerator has been particularly noted. In greater amounts, the bis-(2,5-polythio-1,3,4-thiadiazoles) may function as a sulfur donor. Examples of rubbers include substituted and unsubstituted, saturated and unsaturated, natural and synthetic polymers. The natural polymers include natural rubber in its various forms, e.g., pale crepe and smoked sheet, and balata and gutta percha. The synthetic polymers are derived from a diene monomer and include those prepared from a single monomer (homopolymer) or a mixture of two or more copolymerizable monomers (copolymer) when the monomers are combined in the random distribution or block form. The monomers may be substituted or unsubstituted and may possess one or more double bonds, conjugated and nonconjugated dienes and monoolefins, including cyclic and acyclic monoolefins, especially vinyl and vinylidene monomers. Examples of conjugated dienes are 1,3-butadiene, isoprene, chloroprene, 2-ethyl-1,3-butadiene, 2,3-dimethyl-1,3-butadiene and piperylene. Examples of nonconjugated dienes are 1,4-pentadiene, 1,4-hexadiene, 1,5-hexadiene, dicyclopentadiene, 1,5-cyclooctadiene, and ethyldiene norbornene. Examples of acyclic monoolefins are ethylene, propylene, 1-butene, isobutylene, 1-pentene and 1-hexene. Examples of cyclic monoolefins are cyclopentene, cyclohexene, cycloheptene, cyclooctene and 4-methyl-cyclooctene. Examples of vinyl monomers are styrene, acrylonitrile, acrylic acid, ethylacrylate, vinyl chloride, butylacrylate, methyl vinyl ether, vinyl acetate and vinyl pyridine. Examples of vinylidene monomers are alpha-methylstyrene, methacrylic acid, methyl methacrylate, itaconic acid, ethyl methacrylate, glycidyl methacrylate and vinylidene chloride. Representative examples of the synthetic polymers used in the practice of this invention are polychloroprene homopolymers of a conjugated 1,3-diene such as isoprene and butadiene, and in particular, polyisoprenes and polybutadienes having essentially all of their repeat units combined in a cis-1,4-structure; and copolymers of a conjugated 1,3-diene such as isoprene and butadiene with up to 50% by weight of at least one copolymerizable monomer, including ethylenically unsaturated monomers such as styrene or acrylonitrile; and butyl rubber, which is a polymerization product of a major proportion of a monoolefin and a minor proportion of a diolefin such as butadiene or isoprene. The rubber stocks which may be used with the bis-(2,5-polythio-1,3,4-thiadiazoles) preferably contain cis-1,4-polyisoprene (natural or synthetic), polybutadiene, polychloroprene and the copolymers of isoprene and butadiene, copolymers of acrylonitrile and butadiene, copolymers of acrylonitrile and isoprene, copolymers of styrene, butadiene and isoprene, copolymers of styrene and butadiene and blends thereof.

One advantage of the present invention is that the bis-(2,5-polythio-1,3,4-thiadiazoles) function as curative agents for rubber stocks and are believed to not form nitrosoamines. The bis-(2,5-polythio-1,3,4-thiadiazoles) also function as sulfur donors in an activated nonblooming form. Therefore, the bis-(2,5-polythio-1,3,4-thiadiazoles) may be used in their own right as a rubber curative or as a co-agent in a cure system. While the amount of bis-(2,5-polythio-1,3,4-thiadiazole) that is used in a rubber stock may vary, it generally ranges from about 0.10 phr (parts by weight per 100 parts by weight of rubber) to about 10 phr. Preferably, the amount which is used ranges from about 0.25 phr to about 1.0 phr.

As known to one skilled in the art, in order to cure a rubber stock, one needs to have a sulfur vulcanizing agent. In accordance with one embodiment, the bis-(2,5-polythio-1,3,4-thiadiazole) can function as the sulfur vulcanizing agent in whole or in part with conventional sulfur vulcanizing agents. Examples of suitable conventional sulfur vulcanizing agents which may be used include elemental sulfur (free sulfur) or a sulfur donating vulcanizing agent, for example, an amine disulfide, polymeric polysulfide or sulfur olefin adducts. Preferably, the conventional sulfur vulcanizing agent is elemental sulfur. The amount of sulfur vulcanizing agent will vary depending on the components of the rubber stock and the particular type of sulfur vulcanizing agent that is used. Generally speaking the amount of sulfur vulcanizing agent ranges in an amount of from about 0.25 to about 10 phr. Preferably, the sulfur vulcanizing agent is present in an amount ranging from about 1.0 to about 6.0 phr.

Conventional rubber additives may also be incorporated in the rubber stock. The additives commonly used in rubber stocks include fillers, plasticizers, processing oils, retarders, antiozonants, antioxidants and the like. The total amount of filler that may be used may range from about 30 to about 80 phr, with a range of from about 45 to about 70 phr being preferred. Fillers include silicas, clays, calcium carbonate, calcium silicate, titanium dioxide and carbon black. HAF Black (N-330) and GPF-Black (N-660) are commonly used in rubber stocks intended for use as wire coats or carcass ply coats. Preferably, at least a portion of the filler is carbon black. Plasticizers are conventionally used in amounts ranging from about 2 to about 50 phr with a range of about 5 to about 30 phr being preferred. The amount of plasticizer used will depend upon the softening effect desired. Examples of suitable plasticizers include aromatic extract oils, petroleum softeners including asphaltenes, saturated and unsaturated hydrocarbons and nitrogen bases, coal tar products, cumarone-indene resins and esters such as dibutylphthalate and tricresyl phosphate. Materials used in compounding which function as an accelerator-activator include metal oxides such as zinc oxide, magnesium oxide and litharge which are used in conjunction with acidic materials such as fatty acid, for example, stearic acid, oleic acid, murastic acid, and the like. The amount of the metal oxide may range from about 1 to about 10 phr with a range of from about 2 to about 8 phr being preferred. The amount of fatty acid which may be used may range from about 0.25 phr to about 5.0 phr with a range of from about 0.5 phr to about 2 phr being preferred.

A class of compounding materials known as scorch retarders are commonly used. Phthalic anhydride, salicyclic acid, sodium acetate and N-cyclohexyl thiophthalimide are known retarders. Retarders are generally used in an amount ranging from about 0.1 to 0.5 phr.

Preformed phenol-formaldehyde type resins which may be used in the rubber stock and are generally present in an amount ranging from about 1.0 to about 5.0 phr, with a range of from about 1.5 to about 3.5 phr being preferred.

Conventionally, antioxidants and sometimes antiozonants, hereinafter referred to as antidegradants, are added to rubber stocks. Representative antidegradants include monophenols, bisphenols, thiobisphenols, polyphenols, hydroquinone derivatives, phosphites, thioesters, naphthyl amines, diphenyl-p-phenylenediamines, diphenylamines and other diaryl amine derivatives, para-phenylenediamines, quinolines and mixtures thereof. Specific examples of such antidegradants are disclosed in The Vanderbilt Rubber Handbook (1990), pages 282-286. Antidegradants are generally used in amounts from about 0.25 to about 5.0 phr with a range of from about 1.0 to about 3.0 phr being preferred.

The present invention may be better understood by reference to the following examples in which the parts or percentages are by weight unless otherwise indicated.

EXAMPLE 1

Preparation of Bis(2,5-tetrathio-1,3,4-thiadiazole)

In a 1000 milliliter reaction flask, a mixture of 30 grams (0.20 mole) of 2,5-dimercapto-1,3,4-thiadiazole and 12.8 grams (0.05 mole) of elemental sulfur was prepared in 250 ml of water. The slurry was stirred at high speed and a pale yellow suspension resulted. To the slurry was added 29.4 grams (0.259 mole) of 30% hydrogen peroxide over a five minute period. During the addition of the peroxide, the temperature increased to 38° C. and the reaction slurry became thicker and bright orange. The slurry was stirred with heating until a temperature of 70° C. was obtained. Heating at 70° C. was continued for one hour. During this heating period, the solids turned white. The heating was increased to 100° C. and stirring continued for 5 hours. The solids were collected by suction filtering and dried in a vacuum oven. 40.2 grams of product were recovered (94.8% yield). The product exhibited shrinkage at 145° to 155° C., followed by an amorphous state at 156° to 170° C. and decomposed with gassing at 171° to 175° C.

EXAMPLE 2

Preparation of Bis(2,5-hexathio-1,3,4-thiadiazole)

In a 12 liter round bottom wide mouth flask equipped with a mechanical mixer, a mixture of 900 grams (6.0 mole) of 2,5-dimercapto-1,3,4-thiadiazole and 768 grams (3 mole) of elemental sulfur was prepared in 4 liters of water. The slurry was stirred at high speed and a pale yellow suspension resulted. To the slurry was added 850 grams (7.5 mole) of 30% hydrogen peroxide over a thirty minute period maintaining a reaction of 60° C. The reaction slurry became thicker and dark yellow. The slurry was stirred with heating until a temperature of 95° C. was obtained. Heating at 95° C. was continued for two hours. The mixture was allowed to cool overnight and the solids were collected by suction filtering. The solids were washed with water and then dried. 1620.3 grams of product were recovered (97.8% yield). The product exhibited shrinkage at 145° to 150° C., followed by an amorphous state at 150° to 155° C. and decomposed with gassing at 156° to 172° C.

EXAMPLE 3

Preparation of Bis(2,5-decathio-1,3,4-thiadiazole)

In a 12 liter round bottom wide mouth flask equipped with a mechanical stirrer, a mixture of 900 grams (6 mole) of 2,5-dimercapto-1,3,4-thiadiazole and 1536 grams (6 mole) of elemental sulfur was prepared in 4 liters of water. The slurry was stirred at high speed and a pale yellow suspension resulted. To the slurry was added 850 grams (7.5 mole) of 30% hydrogen peroxide over a thirty minute period maintaining a reaction temperature of 60° C. The reaction slurry became thicker and dark yellow. The slurry was stirred with heating until a temperature of 95° C. was obtained. Heating at 95° C. was continued for two hours. The mixture was allowed to cool overnight and the solids were collected by suction filtering. The solids were washed with water and then dried. 2392.5 grams of product were recovered (98.7% yield). The product exhibited shrinkage at 145° to 155° C., followed by an amorphous state of 156° to 160° C. and decomposed with gassing at 161° to 175° C.

EXAMPLE 5

Physical Testing

Table I below shows the basic rubber stock that was used in this example. The rubber compound was prepared in a two-stage Banbury mix. All parts and percentages are by weight unless otherwise noted. The cure data as well as other physical data for each sample are listed in Table II or Table III.

TABLE I

| Non-Productive | |
|---|---|
| Natural Rubber | 100 |
| Carbon Black | 50 |
| Wax | 1 |
| Antidegradant | 3 |
| Zinc Oxide | 3 |
| Fatty Acid | 2 |
| Productive | |
| Sulfur | 1 |
| Accelerator | 0.75 |
| Retarder | 0.2 |
| Bis-(2,5-polythio-1,3,4-thiadiazole) | Varied |

Cure properties were determined using a Monsanto oscillating disc rheometer which was operated at a temperature of 150° C. and at a frequency of 1.7 hertz. A description of oscillating disc rheometers can be found in the Vanderbilt Rubber Handbook edited by Robert O. Ohm (Norwalk, Conn., R. T. Vanderbilt Company, Inc., 1990), pages 554-557. The use of this cure meter and standardized values read from the curve are specified in ASTM D-2084. A typical cure curve obtained on an oscillating disc rheometer is shown on page 555 of the 1990 edition of the Vanderbilt Rubber Handbook.

In such an oscillating disc rheometer, compounded rubber samples are subjected to an oscillating shearing action of constant amplitude. The torque of the oscillating disc embedded in the stock that is being tested that is required to oscillate the rotor at the vulcanization temperature is measured. The values obtained using this cure test are very significant since changes in the rubber or the compounding recipe are very readily detected. It is obvious that it is normally advantageous to have a fast cure rate.

The following tables report cure properties that were determined from cure curves that were obtained for the rubber stocks that were prepared. These properties include a torque minimum (Min. Torque), a torque maximum (Max. Torque), minutes to 25% of the torque increase (t25), minutes to 90% of the torque increase (t90) and difference between the maximum torque and minimum torque (delta torque).

Peel adhesion testing was done to determine the interfacial adhesion between various rubber formulations that were prepared. The interfacial adhesion was determined by pulling one compound away from another at a right angle to the untorn test specimen with the two ends being pulled apart at a 180 degree angle to each other using an Instron machine. The area of contact was determined from placement of a Mylar sheet between the compounds during cure. A window in the Mylar allowed the two materials to come into contact with each other during testing.

The amount of heat buildup was measured with the Goodrich Flexometer as described in ASTM Designation D623 (Method A). This test is described at pages 530–531 of The Vanderbilt Rubber Handbook, 13th Edition (1990).

The Mooney viscosity was measured at 100° C. in accordance with the equipment and method described at pages 565–566 of The Vanderbilt Rubber Handbook, 13th Edition (1990).

The abrasion resistance was measured in accordance with German DIN 53516 (DIN Abrasion).

Shore Hardness was determined in accordance with ASTM-1415.

Table II indicates the amounts of bis-(2,5-polythio-1,3,4-thiadiazole) that was used in each sample. The bis-(2,5-polythio-1,3,4-thiadiazole) was added to the rubber stocks in the productive stage.

TABLE II

|  | Control Sample 1 | Sample 2 | Sample 3 | Sample 4 |
|---|---|---|---|---|
| Bis(2,5-tetrathio-1,3,4-thiadiazole) (phr) | 0 | 1.0 | 2.0 | 3.0 |
| Monsanto Fatigue (k · cycles) | 345 | 371 | 375 | 330 |
| Rheometer | | | | |
| Torque Rate (slope) | 3.55 | 3.46 | 3.18 | 3.15 |
| Delta Torque (min.) | 28.0 | 29.5 | 31.5 | 32.50 |
| T 25 (min.) | 8.5 | 3.44 | 3.10 | 2.95 |
| T 90 (min.) | 13.3 | 8.34 | 9.15 | 10.25 |
| Stress Strain | | | | |
| 300% Modulus (MPa) | 12.96 | 13.95 | 13.70 | 14.00 |
| Break Strength (MPa) | 25.88 | 23.50 | 22.75 | 22.81 |
| % Elongation | 525 | 510 | 485 | 465 |
| Hardness, RT | 64 | 64 | 66 | 67 |
| Zwick Rebound | 61 | 63 | 63 | 65 |
| Peel Adhesion (Newtons/mm) | 50 | 40 | 35 | 33 |
| Mooney Viscosity (%) | 67 | 65 | 67 | 66 |
| Goodrich Flex | | | | |
| Hardness (Shore A) | 64 | 68 | 70 | 69 |
| Compression Set (%) | 2.1 | 2.0 | 2.0 | 1.8 |
| Heat Build-up (°C.) | 39 | 32 | 32 | 30 |
| DIN Abrasion (mm$^3$) | 131 | 118 | 117 | 127 |

TABLE III

|  | Control Sample 1 | Sample 2 | Sample 3 | Sample 4 | Sample 5 | Sample 6 | Sample 7 |
|---|---|---|---|---|---|---|---|
| Bis(2,5-hexathio-1,3,4-thiadiazole) (phr) | 0 | 1.0 | 2.0 | 3.0 | 0 | 0 | 0 |
| Bis(2,5-decathio-1,3,4-thiadiazole) (phr) | 0 | 0 | 0 | 0 | 1.0 | 2.0 | 3.0 |
| Monsanto Fatigue (k · cycles) | 440 | 361 | 331 | 209 | 374 | 201 | 193 |
| Rheometer | | | | | | | |
| Torque Rate (slope) | 3.25 | 3.75 | 3.84 | 3.41 | 4.00 | 4.25 | 3.70 |
| Delta Torque (min.) | 25.60 | 30.0 | 34.0 | 35.0 | 33.5 | 40.0 | 40.1 |
| T 25 (min.) | 7.35 | 3.7 | 3.2 | 3.0 | 4.0 | 3.25 | 3.1 |
| Stress Strain | | | | | | | |
| 300% Modulus (MPa) | 11.50 | 13.25 | 14.16 | 14.09 | 13.82 | 15.75 | 16.33 |
| Break Strength (MPa) | 24.50 | 23.60 | 23.30 | 23.12 | 24.00 | 22.00 | 23.00 |
| % Elongation | 550 | 500 | 475 | 480 | 500 | 425 | 430 |
| Hardness, RT | 62 | 65 | 67 | 67 | 66 | 69 | 70 |
| Zwick Rebound | 60 | 63 | 64 | 65 | 64 | 66 | 67 |
| Mooney Viscosity (%) | 70 | 68 | 68 | 69 | 69 | 60 | 63 |
| Goodrich Flex | | | | | | | |
| Hardness (Shore A) | 65 | 69 | 70 | 70 | 69 | 72 | 73 |
| Compression Set (%) | 2.4 | 2.1 | 1.6 | 1.7 | 1.7 | 1.8 | 1.4 |
| Heat Build-up (°C.) | 62 | 58 | 54 | 54 | 56 | 56 | 56 |
| DIN Abrasion (mm$^3$) | 125 | 112 | 112 | 118 | 109 | 122 | 128 |
| Peel Adhesion (Newtons/mm) | 52.5 | 40.5 | 29.5 | 28.5 | 39 | 25.25 | 18.75 |

As can be seen above, addition of bis(2,5-tetrathio-1,3,4-thiadiazole) to a rubber stock will result in an increase in the compound state of cure as measured by the increase in the Monsanto rheometer torque increase. This indicates an increase in the compound formulation crosslink density. The compound tensile strength and modulus at 300% elongation is increased along with an increase in the compound resilience or rebound characteristics. In addition heat build-up within the compound is reduced along with a directional improvement in abrasion resistance. These properties collectively will allow improvement in tire performance especially with regard to tread wear and rolling resistance. Similar trends are evident with use of bis(2,5-hexathio-1,3,4-thiadiazole) and bis(2,5-decathio-1,3,4-thiadiazole) such as: an increase in the state of cure and crosslink density, an increase in compound 300% modulus, an improvement in hysteretic properties of the compound as measured by increase in compound rebound, and decrease in compound compression set. In all cases use of these materials leads to improvement in abrasion resistance. In summary, when compounded for application in a rubber stock for use in a product such as a tire, the claimed materials will contribute toward an improvement in the product's performance. For tires, this will represent itself in improved tread wear, reduced rolling resistance performance, and reduction in tire service temperatures.

What is claimed is:

1. Bis-(2,5-polythio-1,3,4-thiadiazoles) consisting of the formula:

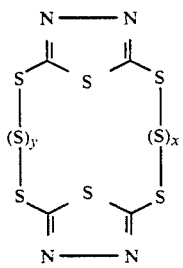

wherein y and x are independently selected from the group consisting of integers of from 2 to 4.

2. The bis-(2,5-polythio-1,3,4-thiadiazoles) of claim 1 wherein x and y are 2.

3. The bis-(2,5-polythio-1,3,4-thiadiazole) of claim 1 wherein the molecular weight ranges from about 424 to 552.

4. A rubber stock comprising:
(a) a rubber selected from the group consisting of natural rubber, a synthetic rubber derived from a diene monomer and mixtures thereof;
(b) from about 0.10 to about 10 phr of a bis-(2,5-polythio-1,3,4-thiadiazole) of the formula:

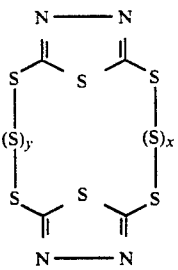

wherein x and y are independently selected from the group consisting of integers of from 2 to 4.

5. The rubber stock of claim 4 wherein said synthetic rubber is selected from the group consisting of cis-1,4-polyisoprene, polybutadiene, polychloroprene, copolymers of isoprene and butadiene, copolymers of acrylonitrile and butadiene, copolymers of acrylonitrile and isoprene, copolymers of styrene, butadiene and isoprene, copolymers of styrene and butadiene and blends thereof.

6. The rubber stock of claim 4 wherein x and y are 2.

7. The rubber stock of claim 4 wherein said bis-(2,5-polythio-1,3,4-thiadiazole) is present in an amount ranging from about 0.25 phr to about 1.0 phr.

8. A process for accelerating the cure rate of a rubber stock comprising admixing (1) a rubber selected from the group consisting of natural rubber, synthetic rubbers derived from a diene monomer and mixtures thereof with (2) a bis-(2,5-polythio-1,3,4-thiadiazole) consisting of the formula:

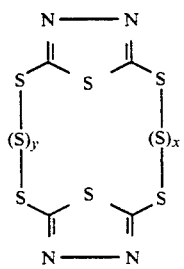

wherein x and y are integers of from 2 to 4.

9. The process of claim 8 wherein from about 0.10 phr to about 10 phr of said bis-(2,5-polythio-1,3,4-thiadiazole) is present.

10. The process of claim 8 wherein from about 0.25 phr to about 1.0 phr is present.

11. The process of claim 8 wherein said synthetic rubber is selected from the group consisting of cis-1,4-polyisoprene, polybutadiene, polychloroprene, copolymers of isoprene and butadiene, copolymers of acrylonitrile and butadiene, copolymers of acrylonitrile and isoprene, copolymers of styrene, butadiene and isoprene, copolymers of styrene and butadiene and blends thereof.

* * * * *